United States Patent
Martel et al.

(10) Patent No.: US 6,315,480 B1
(45) Date of Patent: Nov. 13, 2001

(54) DEVICE FOR DIFFUSING ONE OR SEVERAL FLUID PRODUCT DOSES, AND DEVICE FOR APPLYING A TEMPORARY ADHESIVE TATTOO USING SAME

(76) Inventors: Stephane Christopher Martel, 63 rue de plaisance, 92250 La Garenne Colombes; Francois Henri Cathala, 13, rue Eugene Carriere, 75018 Paris; Valerie Frederique Bochenek, 10, rue de Peronne, 80200 Doingt; Valerie Christine Lacombe-Gervaz, 4, Villa Gaudelet, F-75011 Paris, all of (FR)

( * ) Notice: Subject to any disclaimer, the term of this patent is extended or adjusted under 35 U.S.C. 154(b) by 0 days.

(21) Appl. No.: 09/402,803
(22) PCT Filed: Apr. 9, 1998
(86) PCT No.: PCT/FR98/00724
  § 371 Date: Jan. 6, 2000
  § 102(e) Date: Jan. 6, 2000
(87) PCT Pub. No.: WO98/45127
  PCT Pub. Date: Oct. 15, 1998

(30) Foreign Application Priority Data

| Apr. 10, 1997 | (FR) | 97 04390 |
| Apr. 29, 1997 | (FR) | 97 05261 |
| May 14, 1997 | (FR) | 97 05896 |
| Jan. 20, 1998 | (FR) | 98 00562 |
| Jan. 29, 1998 | (FR) | 98 01003 |

(51) Int. Cl.⁷ .................................................. B43K 5/14
(52) U.S. Cl. ........................ 401/132; 401/205; 401/263
(58) Field of Search ................................ 401/132, 133, 401/134, 135, 205, 201, 261, 263, 264

(56) References Cited

U.S. PATENT DOCUMENTS

| 4,493,574 | * | 1/1985 | Redmond et al. | 401/132 |
| 4,812,067 | * | 3/1989 | Brown et al. | 401/132 |
| 5,928,797 | * | 7/1999 | Vineberg | 401/132 |
| 6,007,264 | * | 12/1999 | Koptis | 401/132 |

FOREIGN PATENT DOCUMENTS

WO 94/12071 * 6/1994 (WO) .............................. 401/132

* cited by examiner

Primary Examiner—David J. Walczak
(74) Attorney, Agent, or Firm—Michael Best & Friedrich LLP (57) ABSTRACT

A device for diffusing one or several fluid product doses, each dose being contained in a sealed reserve defined by an envelope made of a flexible and ductile material, such that a collapsing pressure applied on the reserve causes the envelope to burst open releasing the product contained in the reserve. The envelope is locally provided with at least a weakened zone forming a pre-opening, so as to cause the envelope to burst open at the pre-opening, thereby channelling the product through the pre-opening in a predetermined direction.

28 Claims, 5 Drawing Sheets

DEVICE FOR DIFFUSING ONE OR SEVERAL FLUID PRODUCT DOSES, AND DEVICE FOR APPLYING A TEMPORARY ADHESIVE TATTOO USING SAME

The present invention relates to a device for delivering one or more doses of a fluid product, such as a liquid, creamy, gelatinous or gaseous product, as well as to a device for the application of an adhesive temporary tattoo using the aforementioned delivery device. The delivery device of the invention applies especially to the delivery of a pharmaceutical, cosmetic, food, hygiene, perfumery and household-cleaning product.

In the field of perfumery and cosmetics, it is common practice to distribute free samples to the public which contain a small dose of products, in order to promote the product and to satisfy the public's craze for this type of sample. These product samples are generally packaged in small bottles or sachets which are provided with a removable stopper, with a spray device, with a tearable tab or with a breaking line for delivering the product. These delivery means have a relatively high manufacturing cost given that they are used only once, they are difficult to handle and, furthermore, run the risk of injuring the user.

A known device of this kind comprises a plastic package or a blister pack defining one or more cavities containing a generally liquid product, the package or the blister pack having a tab intended to be broken by bending, in order to gain access to the cavity.

Another known device comprises a first moulded plastic film defining a cavity for housing the product therein and a second film closing off the said cavity, it being possible to remove or tear the said second film in order to gain access to the cavity.

Blister packs of this type are also used for packaging medicines in the form of tablets or capsules, as well as for packaging soft contact lenses.

Also known, in the food field, are tearable plastic sachets intended to contain a dose of tomato sauce or salad dressing.

In the hotel industry, such sachets are also used to provide customers with independent doses of shampoo or liquid soap.

It will also be noted that such a device can be used for containing deodorizing doses for diffusing a perfumed gaseous product contained in a sachet or bottle into the ambient air. It will be noted that the device of the invention may be inserted into a magazine.

Document FR-A-2,632,936 describes a device for delivering a liquid or semi-liquid cosmetic product, this device consisting of a relatively thin film of plastic which defines a small sealed volume in which a product dose is packaged, this dose being able to be released by crushing the said volume by pressing it with one's fingers. However, this plastic film of generally spherical shape bursts in one's fingers when it is being crushed, making its use unpleasant for the user who will have his or her fingers impregnated with product.

The object of the invention is to eliminate the aforementioned drawbacks and to provide a device for delivering one or more doses of a fluid product, which is simple to use, inexpensive to manufacture, effective in operation, compact and lighter in weight and which minimizes product wastage during delivery.

For this purpose, the subject of the invention is a device for delivering one or more doses of a fluid product, each dose being contained in a sealed reserve which is defined by an envelope at least partially made of a deformable flexible material, so that a crushing pressure exerted on the reserve causes the envelope to burst in order to release the product contained in the reserve, characterized in that the envelope is provided locally with at least one region of weakness forming a pre-aperture, so as to cause the envelope to burst instantly at the pre-aperture, the flow of product thus being channelled by the pre-aperture in a predetermined orientation. By virtue of the invention, the product is no longer delivered directly in contact with one's fingers, thereby avoiding one's fingers getting dirty and eliminating the risk of injury. Furthermore, since the flow of product is directed in a selected orientation, it is possible to optimize the use of the product to be delivered, without unnecessary product wastage. Since the product is delivered simply by pressing on the device, its use will be facilitated and speeded up.

Advantageously, the envelope comprises two films made of a plastic or the like, which are hermetically bonded to each other, for example by adhesive bonding or heat sealing, in a peripheral region in order to define, between the two films, the reserve containing the product.

In a first embodiment, the pre-aperture consists of a prescoring of the envelope, preferably in the general form of a cross. In another embodiment, the pre-aperture consists of a region of smaller thickness, preferably by local deformation of the envelope.

In yet another embodiment, the peripheral bonding region comprises locally a weakened heat-sealing region forming the aforementioned pre-aperture, while the rest of the peripheral bonding region is a definitive heat-sealing weld. Advantageously, the weakened heat-sealing region is defined between a peripheral portion in the form of a tab of one of the films and a corresponding portion of the other film, the said portions being superposed and extending some considerable distance away from the peripheral edge of the reserve.

In a first variant, the aforementioned tab projects into the reserve and is heat sealed in a detachable manner to a corresponding portion of the other film, which has an orifice for delivering the product to the outside when the tab becomes detached under the effect of the pressure of crushing the reserve.

In another variant, the tab projects outside the reserve and is heat sealed in a detachable manner to a corresponding portion of the other film, apart from two lateral edges of the tab which are heat sealed in a definitive manner to the other film in order to define at least one prechannel for opening the reserve.

In a first embodiment, the distal end edge of the tab is welded in a detachable manner in order to define at least one prechannel which can be opened at the end in order to expel the product. In this case, the tab may be extended beyond the corresponding portion of the other film, so as to be able to fold over and fasten in a detachable manner the projecting portion of the tab to the other film, in order to isolate the passage for expelling the product, before its use, from external contaminants.

In another embodiment, the distal end edge of the tab is heat sealed in a definitive manner to the other film, in order to define at least one closed prechannel, and at least one orifice is made through the tab and/or the corresponding portion of the other film in order to expel the product when the weakened heat-sealing weld becomes detached under the effect of the pressure exerted on the reserve.

According to another characteristic, each expulsion orifice may include a projecting end-piece in order to define a nozzle for spraying the product.

According to yet another characteristic, each orifice may be covered with a protective film, which can be moved aside under the effect of the pressure of the product leaving via the orifice, so as to isolate the orifice from external contaminants before use.

Advantageously, the expulsion orifice may consist of a plurality of micro-orifices, arranged for example in the form of a star, in order to spray the product when it is expelled.

According to yet another characteristic, the tab includes at least one intermediate line of definitive welding to the other film between its definitively heat-sealed lateral edges, the said intermediate line of welding being approximately parallel to the said lateral edges in order to define a plurality of prechannels for delivering the product.

In one particular embodiment of the device, the reserve is in the general form of a hollow bubble containing the product to be delivered.

In another embodiment, the two films forming the reserve are more or less plane and are superposed, at least one of them including an outwardly domed region, obtained for example by a moulding, in order to define with the other film the aforementioned reserve, the peripheral region of the films around the said domed region extending approximately in the same plane in order to define a peripheral surface for supporting and gripping the device.

In a variant, the two films include a common line of bending which passes right in line with the pre-aperture of the reserve, so that by exerting pressure on the peripheral surface for supporting the device, on either side of the common line of bending, the reserve is crushed by being pinched between the two folded-over parts of the device, thereby causing the product to be delivered via the pre-aperture located on the edge of the dihedron formed by the two folded-over parts of the device.

According to another characteristic, the film which is provided with a pre-aperture includes, on its external face, a layer of material forming an applicator pad which is hermetically bonded to the periphery of the said support surface, so as to impregnate the applicator pad with the product via the pre-aperture when the reserve is burst, the applicator pad serving to apply the product to any chosen surface, it being possible for the applicator to be an absorbent paper or a spongy or cottony textile material. In this case, an intercalar free space may be provided between the applicator pad and the facing film in order to allow the product released by the reserve to spread out uniformly over the entire surface of the applicator pad.

Advantageously, a protective film which can be moved aside and is bonded to one of the edges of the applicator pad on its external face may be provided, in order to cover the pad and isolate it from any external element that might damage and/or contaminate it.

Preferably, the pre-aperture is located on one of the films, approximately at the centre of the reserve.

The reserve may contain a liquid, creamy, gelatinous or gaseous product.

A second subject of the invention relates to a device for applying an adhesive temporary tattoo.

A device is known, from U.S. Pat. No. 5,578,353, for the transfer printing of a ticket bearing an ink, using a wet sponge or a spray applied to the skin. However, such a device requires the use of a wet sponge or of another equivalent instrument, thereby complicating the use.

Document DE-A-19606839 describes a device comprising an auxiliary support, a layer of contact adhesive and a transfer layer between the support and the layer of adhesive, the said transfer layer containing a binder which adheres more strongly to the adhesive layer than to the support, the transfer layer and/or the layer of adhesive having, on the one hand, fine hollow particles containing water and, on the other hand, a solid alcohol soluble in water, so that pressure exerted on the support causes the microparticles to burst in order to apply the said transfer layer to a surface. However, such a device requires the manufacture of microspheres in an opaque polymer layer, the said opaque polymer layer being intended to be transferred to the surface, thereby complicating the manufacture and increasing the production costs.

The second object of the invention is to eliminate the aforementioned drawbacks of the prior devices for an adhesive temporary tattoo and to provide a device for applying the adhesive temporary tattoo which is simple and inexpensive to manufacture and which allows the adhesive temporary tattoo to be instantly applied to any chosen surface.

For this purpose, the second subject of the invention is a device for applying an adhesive temporary tattoo using the delivery device defined above, characterized in that an ink for the adhesive temporary tattoo is positioned on the external face of the applicator pad so that pressure exerted by the user on the reserve causes the envelope to burst via the pre-aperture, which in turn moistens the applicator pad and instantly transfers the adhesive temporary tattoo onto the chosen surface.

Advantageously, the device includes a protective film which can be moved aside and is bonded to one of the edges of the applicator pad on its external face, in order to cover the ink for the adhesive temporary tattoo and to isolate it from external elements that might contaminate and/or damage it. The protective film may be provided on its external face with a layer of adhesive material covered by a peelable protective film so as to make it possible to transfer the tattoo already applied to a surface, onto the said layer of adhesive material after having peeled the protective film and to apply the said tattoo again to another surface.

According to another characteristic, the device includes an additional film hermetically bonded to the periphery of the support surface, on the opposite side from the pre-aperture, so as to define a volume of air between the said additional film and the reserve, the said additional film having locally a peripheral weakened-bonding region so that crushing pressure exerted on the said additional film causes, successively or simultaneously, the audible bursting of the volume of air in the weakened-bonding region and the bursting of the reserve via the pre-aperture.

The invention will be better understood and further aims, details, features and advantages thereof will appear more clearly in the course of the detailed explanatory description which follows of several currently preferred particular embodiments of the invention, these being given solely by way of non-limiting illustration, with reference to the appended schematic drawings in which.

Figure 1:
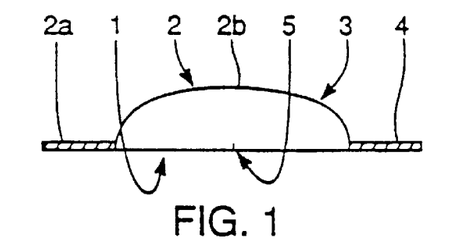
FIG. 1 is schematic cross-sectional view of a first embodiment of the delivery device according to the invention, having a pre-aperture at the centre of one of the films defining the reserve.
Figure 1A:
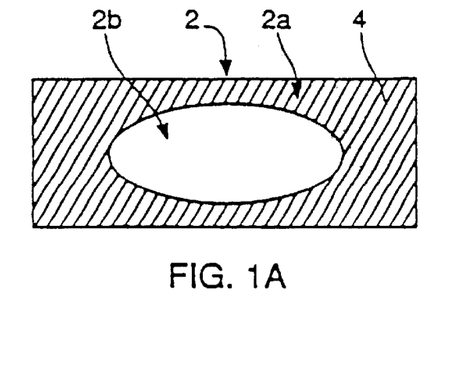
FIG. 1A is a view from below of the device in FIG. 1, the film provided with the pre-aperture being omitted.

FIG. 1 shows, in section, an approximately plane first film 1 to which is applied a second film 2 having a peripheral region 2a which is adhesively bonded or heat sealed to a corresponding peripheral region of the film 1 and an outwardly domed central region 2b, for example obtained by moulding, so as to define, between the said domed central region 2b and the facing film 1, a closed space 3 defining a reserve for a product to be delivered. Indicated by the hatched lines is the adhesive-bonding or heat-sealing region 4. The lower film 1 furthermore has, at its centre, a pre-aperture defined by a prescoring in the form of a cross 5 in order for the product to be delivered to the outside. FIG. 1A shows that the peripheral region 2a of the film 2 is hatched in order to indicate the location of the adhesive bonding or of the heat sealing 4. The general shape of the device is approximately rectangular, whereas the reserve 3 has an elliptical general shape seen from above.

The peripheral region 2a of the film 2 forms with the corresponding portion of the film 1 an annular support serving especially for gripping the device.

Figure 2:
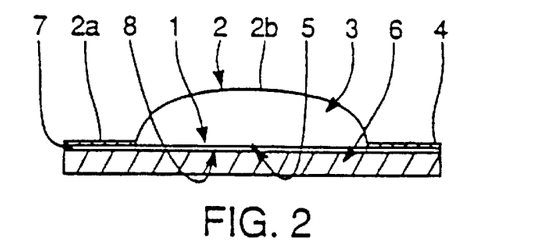
FIG. 2 is a view similar to FIG. 1, the device being furthermore equipped with an applicator pad located facing the pre-aperture.
Figure 2A:
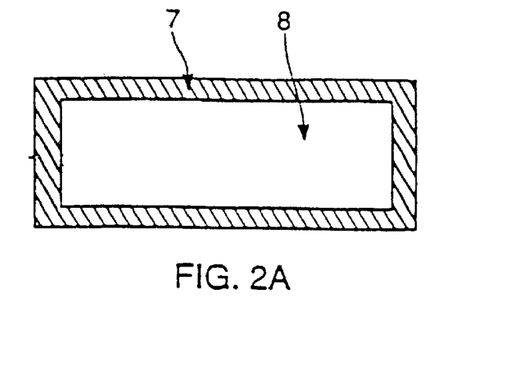
FIG. 2A is a view from above of FIG. 2, showing the applicator pad by itself.

Referring now to FIG. 2, this shows that a layer of material 6 forming an applicator pad is peripherally fastened to the external surface of the film 1, by means of a weld bead or bead of adhesive 7, the said bead defining an intercalar space 8 between the pre-aperture 5 of the film 1 and the internal facing surface of the applicator pad 6. This applicator pad 6 may be an absorbent paper or a spongy or cottony textile material. The purpose of the intercalar space 8 is to allow the product contained in the reserve 3 and leaving via the pre-aperture 5 to be delivered over approximately the entire internal surface of the applicator pad 6, in order to allow it to be impregnated with product in an approximately uniform manner. Thus, the product may be applied to any chosen surface by means of the external surface of the applicator pad 6. Of course, the bonded regions 4 and 7 are hermetically sealed with respect to the product to be delivered.

Figure 3:
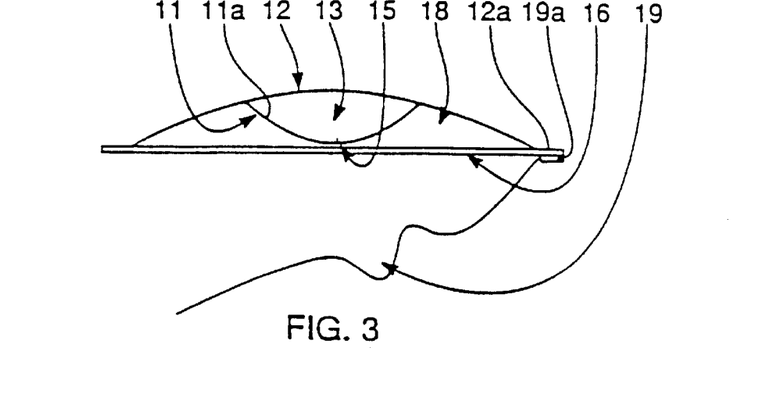
FIG. 3 is an alternative embodiment of the device in FIG. 2, the applicator pad being furthermore provided with a protective film which can be moved aside.

FIG. 3 shows an alternative embodiment in which the upper film 12 has a slight downwardly concave shape and the film 11 more or less follows the shape of the film 12, apart from the central portion 11a which is downwardly domed and provided at its centre with the pre-aperture 15. The reserve 13 here therefore faces downwards, unlike in FIG. 1 where the reserve 3 faced upwards.

Figure 3A:
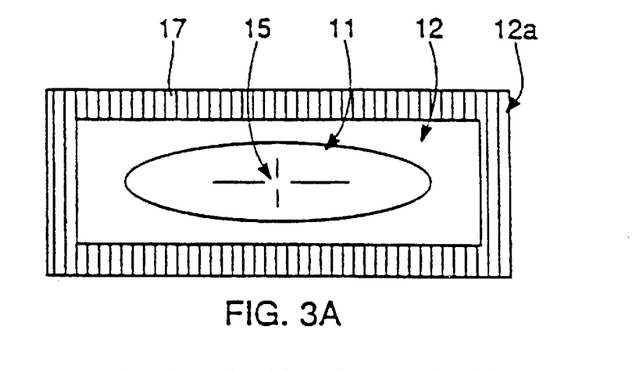
FIG. 3A is a view from below of FIG. 3, the applicator pad being omitted.

The films 11 and 12 are connected around their periphery 12a to an applicator pad 16 via a peripheral weld bead 17 or bead of adhesive (see FIG. 3A). The applicator pad 16 is connected via a transverse edge to a tab 19a of a transparent flexible protective film 19 which is intended to cover the external surface of the applicator pad 16 in order to isolate it from the outside and protect it from any contamination and/or deterioration.

FIG. 3 shows that the intercalar space 18 provided between the reserve 13 and the applicator pad 16 is significantly greater than the intercalar space 8 in FIG. 2, since here the domed surface 11a of the reserve faces the applicator pad.

Figure 4:
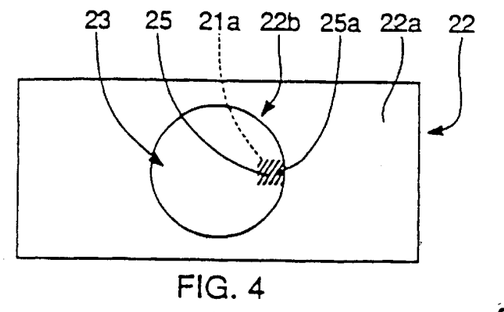
FIG. 4 is a plan view from above of another embodiment of the delivery device according to the invention, the pre-aperture region being defined on an internal peripheral edge of the reserve.

In the variant in FIG. 4, the upper film 22 also has a rectangular shape with a central portion 22b approximately in the form of an outwardly domed spherical cap and a plane peripheral region 22a. The central portion 22b of the film 22 defines, with the lower film (not illustrated), a reserve 23.

The lower film includes an inwardly curved tab 21a which is adhesively bonded or heat sealed, as indicated by the hatched region 25, to the internal surface of the domed portion 22b of the film 22. This tab 21a is hermetically fastened by detachable spots of adhesive or a weakened heat-sealed weld to the portion 22b of the film 22, in order to allow this tab 21a to be detached when pressure is exerted on the reserve 23. When the tab 21a is detached, the product can diffuse towards the outside via an orifice 25a made through the portion 22b of the film 22, right in line with the tab 21a. Before pressure is exerted on the reserve 23, the orifice 25a is hermetically sealed by the weakened bonding 25 to the tab 21a.

As a variant, it would be possible to provide the orifice 25a on the lower film and the tab 21a on the upper film 22, without departing from the scope of the invention.

The only edge of the tab 21a which is not detachable is that which is common to the peripheral edge of the portion 22b of the film 22 which is heat sealed in a definitive manner to the lower film.

Figures 6, 6A, 7:
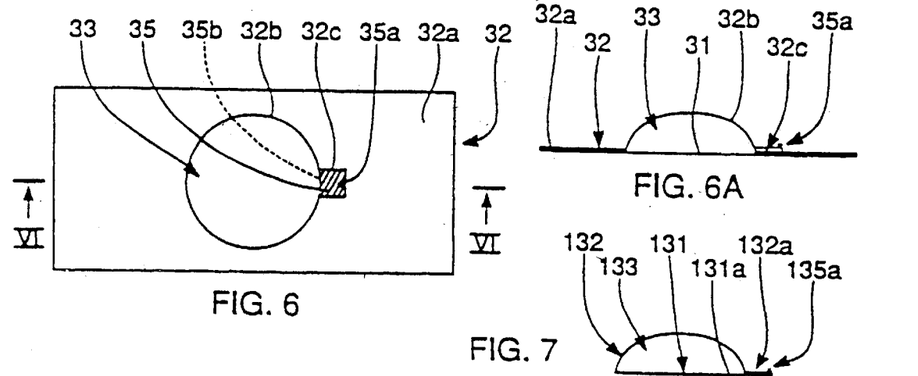
FIG. 6 is an alternative embodiment of the device in FIG. 4, the pre-aperture region being defined on an external peripheral edge of the reserve.
FIG. 6A is a cross-sectional view on the line VI in FIG. 6.
FIG. 7 is a view similar to FIG. 6A, but illustrating the reserve devoid of a surrounding peripheral support.

In the variant in FIG. 6, the upper film 32 also has a central portion 32b in the form of a spherical cap and a surrounding plane portion 32a. The reserve 33 is defined between the domed central portion 32b of the film 32 and the facing internal surface of the lower plane film 31 (see FIG. 6A).

The pre-aperture region 35 (shown hatched) is defined here by a tab 32c forming part of the peripheral portion 32a of the film 32, the said tab 32c extending from a peripheral edge of the central portion 32b and being heat sealed in a definitive manner by all its sides to the lower film 31, apart from its edge 35b common to the peripheral edge of the central portion 32b, which edge 35b is connected by a weakened weld to the lower film 31. The tab 32c is also connected by a weakened heat-sealing weld 35, over its entire surface, to the lower film 31, for the reason explained below. An orifice 35a is made through the tab 32c in order to allow the product to be delivered to the outside when the internal edge 35b and the entire internal surface 35 of the tab 32c is detached from the lower film 31 under the effect of pressure exerted on the reserve 33. The pre-aperture region 35 thus forms a prechannel for expelling the fluid, which prechannel, under the effect of the pressure, expands into a channel by detaching the weakened weld, thereby allowing the fluid contained in the reserve 33 to pass through the channel into the expulsion orifice 35a.

In FIG. 7, the two films 131 and 132 do not have a plane peripheral region but are connected to each other only by their common peripheral edges. In other words, the film 132 has a general shape in the form of a spherical cap and the film 131 has a shape approximately in the form of a flat disc. The film 132 furthermore includes a tab 132a which projects outwards and which is superposed on a corresponding tab 131a which projects to the outside of the film 131. The tab 132a has an orifice or a projecting spray nozzle 135a for the product contained in the reserve 133, the tabs 131a and 132a being bonded by a weakened weld, apart from their external edges which are mutually welded in a definitive manner.

Figure 5:
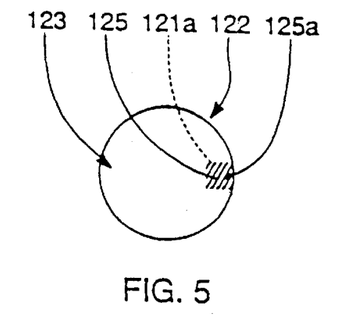
FIG. 5 is a view similar to FIG. 4, the reserve not having a surrounding peripheral support.

FIG. 5 shows the same device as in FIG. 4, except that here it does not include a plane peripheral surface surrounding the reserve 123. The upper film 122 has a general shape in the form of a spherical cap, in a similar manner to the film 132 in FIG. 7. Near its peripheral edge, the film 122 has an orifice 125a which is closed off by an internal tab 121a of the lower film (not illustrated) with a weakened weld 125. The operation of the device in FIG. 5 is identical to that in FIG. 4.

As a variant, the element 22b, 122, 32b and 132 in FIGS. 4 to 7, respectively, may consist of a rigid shell replacing the moulded flexible film, thereby allowing the device to be inserted between the sheets of a journal or magazine by placing it via the film 21, 121, 31 and 131 on a sheet using a detachable adhesive. Thus, there is no risk of the device bursting under the effect of the pressure of the magazine, when transporting and storing it, and the device can be detached in order to reposition it on another support or another chosen surface or in order to make it burst by exerting pressure on the flexible plane film.

Figure 8:
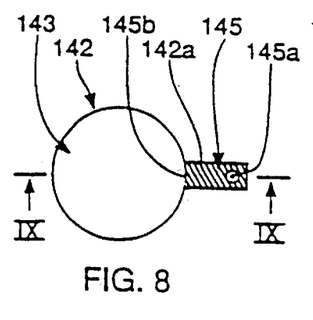
FIG. 8 is a view from above of a device similar to that in FIG. 7, but illustrating a reserve in the general form of a spherical bubble.
Figure 8A:
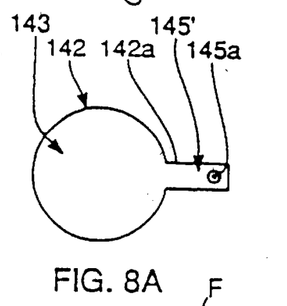
FIG. 8A is a view similar to FIG. 8, demonstrating the detachment of the weakened weld of the device during its use.
Figure 9:
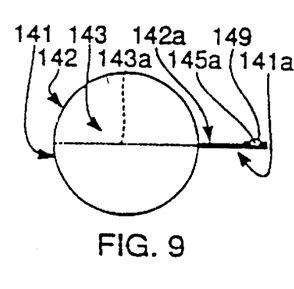
FIGS. 9 and 9A are sectional views on the line IX in FIGS. 8 and 8A, respectively.
Figure 9A:
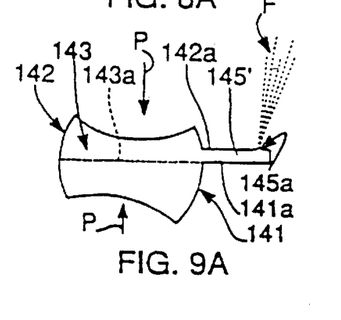

In the embodiment illustrated in FIGS. 8 and 9, the reserve 143 has a spherical general shape obtained by joining two hemispherical films 141 and 142 together along their common equatorial edge 143a. The films 141 and 142 each have a respective tab 141a and 142a which are superposed and project outwards. These tabs 141a and 142a are bonded to each other along their entire sides by a permanent weld, apart from their internal edge 145b and their facing surface 145 which are bonded by a weakened weld, as indicated in the hatched region. The tab 142a and/or the tab 141a have an orifice 145a emerging in the weakened weld region 145 in order to allow the product contained in the reserve 143 to be ejected when the weakened weld region 145 has been detached, forming an ejection channel 145' as illustrated in FIGS. 8A and 9A. This is because, under the effect of a compressive force exerted on each film, as illustrated by the arrows P in FIG. 9A, the weakened weld region 145 becomes detached, forming the channel 145', thereby allowing the fluid to be ejected via the orifice 145a as indicated by the arrow F.

Figure 11:
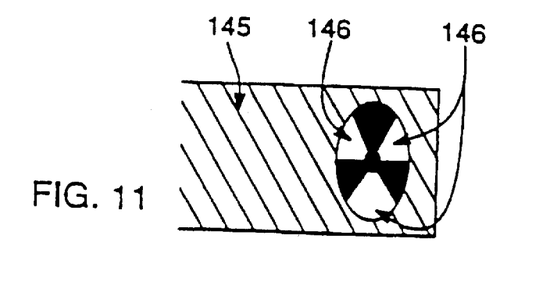
FIG. 11 is a partial and enlarged view of a weakened heat-sealed region incorporating a plurality of micro-orifices that can be used in the embodiment in FIGS. 4 to 10.

Of course, the tab 141a and/or 142a may have several product ejection orifices, as illustrated in FIG. 11. In this figure, several orifices 146 arranged in the form of a star emerge in the weakened weld region 145 in order to produce a spraying effect or microjets of the product contained in the reserve 143.

In FIG. 9, an small additional protective film 149 is adhesively bonded, in a detachable manner, or bonded by a weakened heat-sealing weld to the orifice 145a in order to cover it and isolate it from external contaminants or deteriorating agents, especially for hygiene regions.

Figure 10:
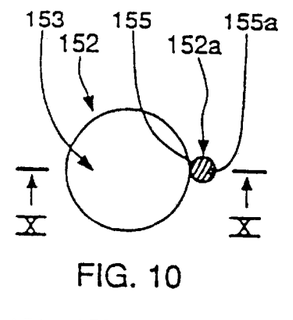
FIGS. 10 and 10A are views similar to FIGS. 8 and 9 respectively, but illustrating an alternative embodiment of the device.
Figure 10A:
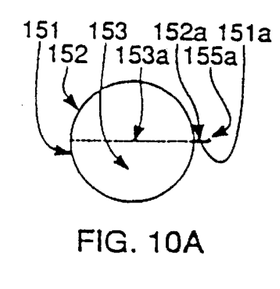

In FIGS. 10 and 10A, the elements which are identical or similar to those illustrated in FIGS. 8 and 9 bear the same reference numbers increased by ten. The variant in FIG. 10 differs from the embodiment in FIGS. 8 and 9 principally by the fact that the tabs 152a and 151a here have a circular general shape instead of the approximately rectangular shape in FIGS. 8 and 9, and by the fact that the expulsion orifice 155a here is in the form of a outwardly projecting nozzle instead of the simple orifice 145a in FIGS. 8 and 9.

Figure 12:
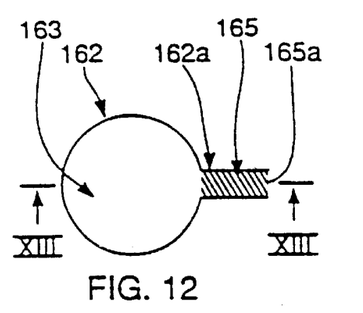
FIGS. 12, 12A, 13, 13A are views similar to FIGS. 8, 8A, 9, 9A respectively, but illustrating an alternative embodiment of the invention.
Figure 12A:
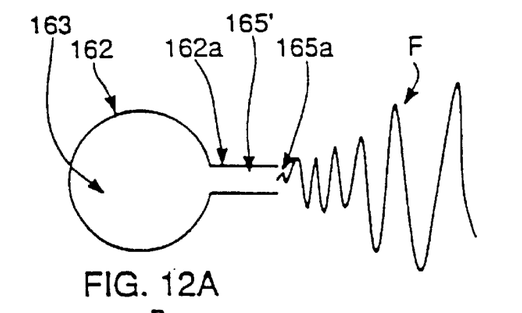
Figure 13:
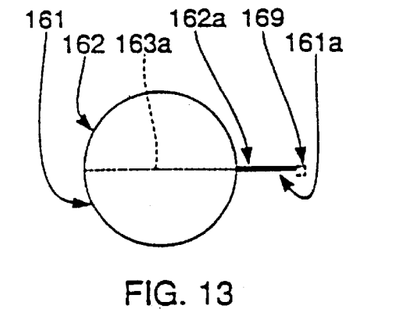

In FIGS. 12 and 13, the elements which are identical or similar to those illustrated in FIGS. 8 and 9 bear the same reference numbers increased by twenty. The variant in FIGS. 12 and 13 differs from the embodiment in FIGS. 8 and 9 essentially by the fact that the orifice for expelling the fluid consists here of the distal edge 165a of the weakened weld region 165 between the tabs 162a and 161a. Consequently, when pressure P is exerted on the reserve 163 the tabs 161a and 162a become detached, defining a discharge channel 165', which emerges on the outside at the tip 165a, in order to eject the product as indicated by the arrow F. Unlike the embodiment in FIGS. 8 and 9 the fluid F in FIGS. 12 and 13 is delivered to the outside without being sprayed. This is quite suitable, for example, for a creamy, gelatinous or pasty product.

Figure 13A:
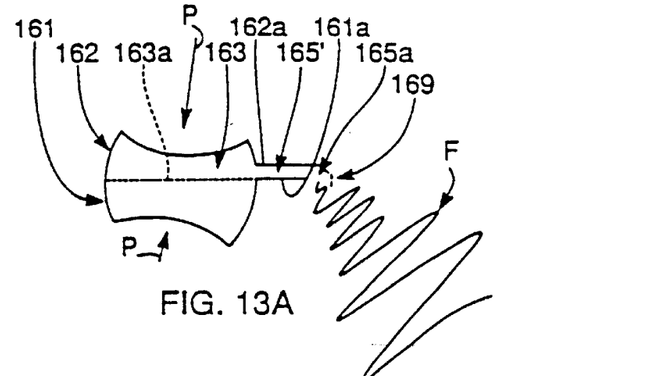

The distal expulsion orifice 165a in FIG. 13 is covered by an extension 169 of the tab 162a so as to be able to fold over and fasten, in a detachable manner the projecting portion of the tab to the other film in order to isolate it from external contaminants and/or deteriorating agents, especially for hygiene reasons. Under the effect of the pressurized fluid ejected via the open channel 165', the extension 169 of the tab 162a becomes detached, as illustrated in FIG. 13A, and also contributes to orientating the flow of product F in a defined direction. The extension 169 could also serve as an applicator.

Figure 14:
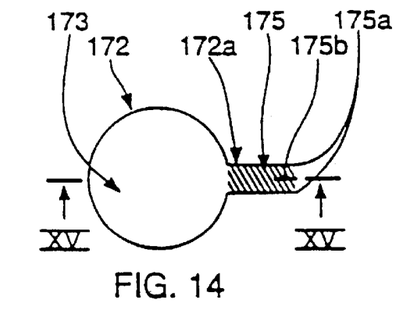
FIGS. 14, 14A, 15 and 15A are similar views to FIGS. 12, 12A, 13 and 13A respectively, but illustrating yet another alternative embodiment.
Figure 14A:
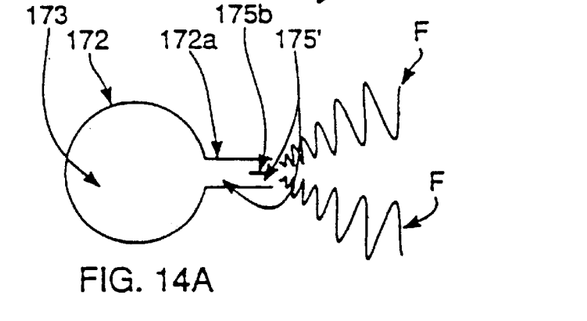
Figure 15:
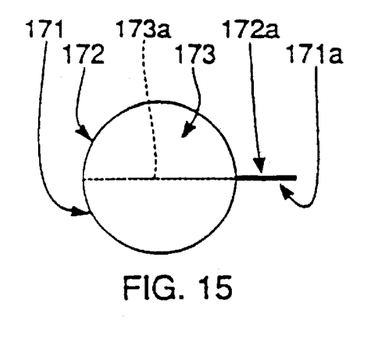
Figure 15A:
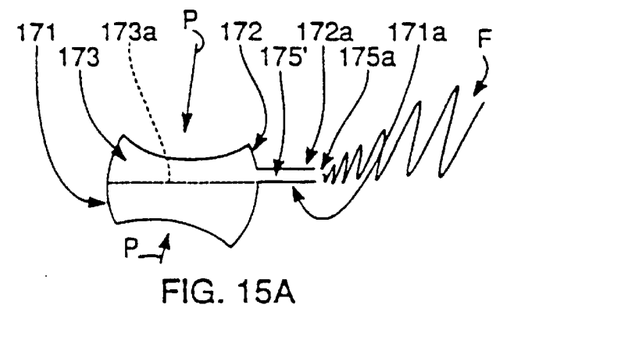

In FIGS. 14 and 15, the elements which are identical or similar to those of the embodiment in FIGS. 12 and 13 bear the same reference numbers increased by ten. The variant in FIGS. 14 and 15 differs essentially from the embodiment in FIGS. 12 and 13 by the fact that the device in FIGS. 14 and 15 has an intermediate line of permanent welding 175*b* in the weakened weld region 175, the said intermediate line of permanent welding 175*b* extending between the lateral edges of the tabs 171*a* and 172*a* and parallel to the latter, so as to define two narrower parallel channels 175' emerging on the outside at the distal end 175*a*, so as to obtain two separate jets of fluid F. Of course, several intermediate lines of permanent welding could be provided in order to obtain several jets of fluid.

Figure 16:
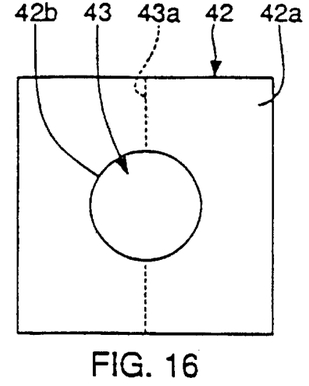
FIGS. 16 and 16A are views, from above and from below respectively, of a device of the type in FIG. 1, in which a common line of bending is formed on the two films right in line with the pre-aperture.
Figure 16A:
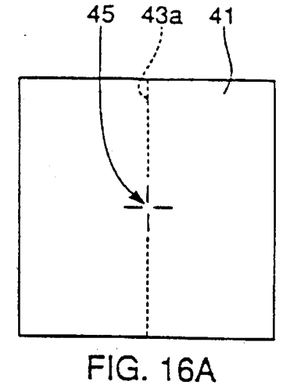
Figure 17:
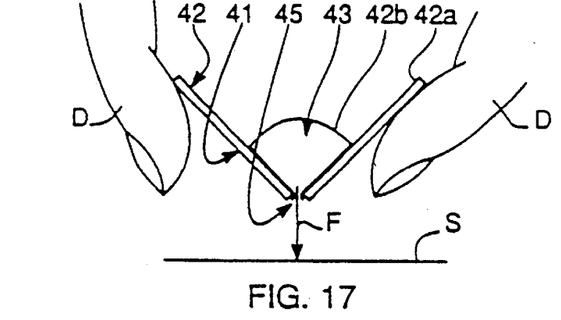
FIG. 17 is a side view of the device in FIG. 16, showing the delivery of the product in a selected orientation onto a chosen surface.

In another embodiment of FIG. 2 illustrated in FIGS. 16 and 17, the device has an upper film 42, a circular central portion 42*b* of which is outwardly domed and joined to a surrounding plane peripheral portion 42*a*, and a square-shaped plane lower film 41 which is permanently fastened to the peripheral plane portion 42*a* of the film 42. The film 41 has, right in line with the domed circular portion 42*b* of the film 42, a prescoring in the form of a cross 45, preferably at the center of the said circular portion 42*b*. The reserve 43 is defined between the domed portion 42*b* and the subjacent lower film 41. The film 41 and the plane peripheral region 42*a* of the film 42 furthermore have a common line of bending 43*a* which extends over their entire length and passes through the pre-aperture 45, thereby dividing the device into two foldable parts. Thus, by exerting pressure with one's fingers D (see FIG. 17) on each foldable part of the device, the reserve 43 is compressed between the two folded parts of the device, thereby causing the reserve to burst via the pre-aperture in order to eject the product in the direction of the arrow F towards a chosen surface S. Under these conditions, the user no longer acts directly on the reserve 43 but on the peripheral parts of the films 41 and 42.

Figure 17A:
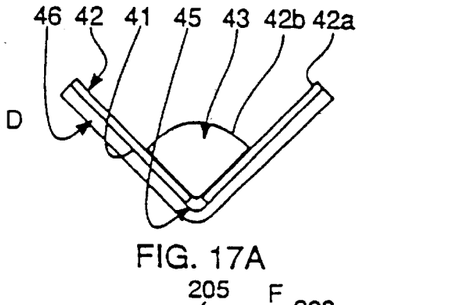
FIG. 17A is a view similar to FIG. 17, the device being furthermore equipped with an applicator pad.

In FIG. 17A, an applicator pad 46 is fastened to the external face of the film 41 in a manner similar to the embodiment in FIG. 2. Thus, the fluid leaving via the pre-aperture 45 will be able to impregnate the applicator pad 46.

Figure 18:
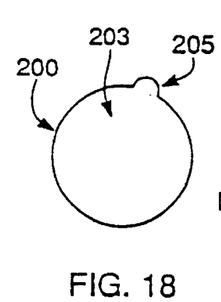
FIG. 18 shows a reserve in the form of a spherical bubble having a pre-aperture consisting of a region of smaller thickness.
Figure 18A:
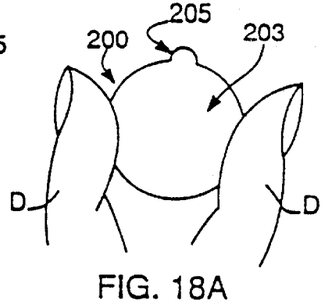
FIGS. 18A and 18B illustrate the bubble in FIG. 18 during two successive steps in its use.
Figure 18B:
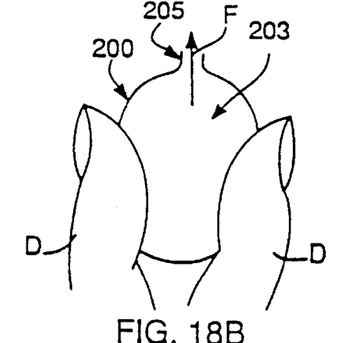

In FIGS. 18, 18*a* and 18*b*, the device consists of a hollow bubble 200 defining, on the inside, a reserve of 203 for the product to be dispensed, the said bubble 200 having locally an outwardly domed deformation 205 of smaller thickness, in order to constitute a weakened region of pre-aperture by bursting. Of course, the bubble 200 could be obtained by joining two heat-sealed hemispherical films together in a definitive manner along their common equatorial edge.

Compressing the bubble 200 with one's fingers D causes the weakened region 205 to burst, in order to eject the product in the direction of the arrow F.

Figure 19:
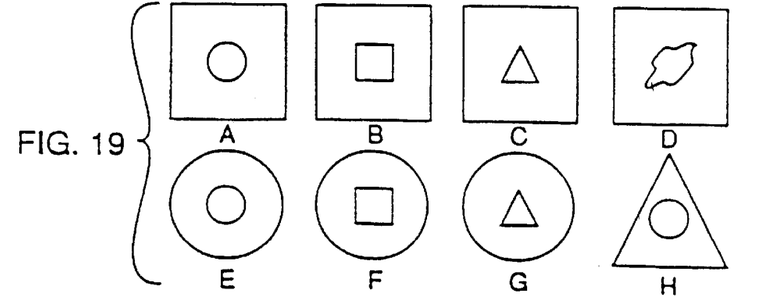
FIGS. 19A to 19H are schematic views from above illustrating various embodiments of the reserve and of the surrounding support of a device according to the invention.

FIGS. 19A to H illustrate various shapes for the reserve and the surrounding support. In FIGS. 19A to D, the support has, seen from above, an approximately square shape while the reserve has circular, square, triangular and irregular shape, respectively. In FIG. 19E to G, the support has a circular shape while the reserves have a circular, square and triangular shape, respectively. In FIG. 19H, the support has a triangular shape and the reserve has a circular shape. However, the respective shapes of the support and of the reserve may vary in any manner, without departing from the scope of the invention.

Figure 20:
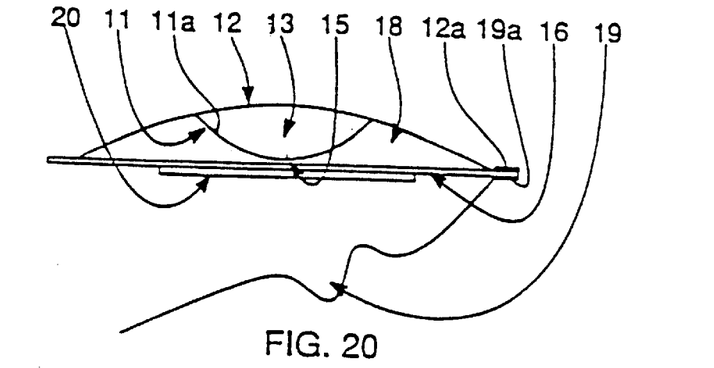
FIG. 20 is a view similar to FIG. 3, but illustrating a device for applying an adhesive temporary tattoo, which furthermore includes an adhesive ink layer on the applicator pad.
Figure 21:
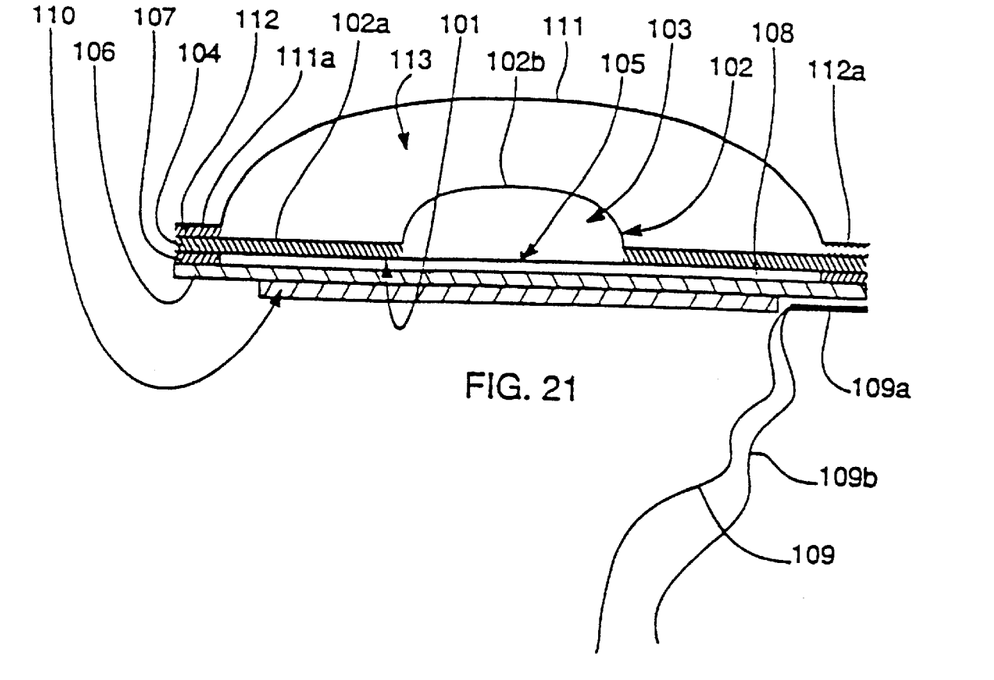
FIG. 21 is a view similar to FIG. 2, but illustrating an alternative embodiment of a device for applying an adhesive temporary tattoo, which furthermore includes an adhesive ink layer, a protective film provided with a peelable film, and an additional film on top of the reserve in order to generate a bursting noise.

Referring now to FIGS. 20 and 21, two particular embodiments of a device for applying an adhesive temporary tattoo will be described.

FIG. 20 is identical to FIG. 3, apart from a layer of ink 20 for an adhesive temporary tattoo, which ink is deposited on the external surface of the applicator pad 16. When pressure is exerted on the film 12 in order to crush the reserve 13, the pre-aperture 15 bursts, thereby releasing the liquid into the intermediate space 18. The ejected liquid then spreads out uniformly over the entire internal surface of the absorbent pad 16, the latter, once wetted, allowing patterns formed by the ink 20 to be transferred onto any chosen surface.

The protective film 19 makes it possible to isolate the adhesive transfer-printing ink 20 from any external deteriorating agent.

In the variant in FIG. 21, the elements which are identical or similar to those illustrated in FIG. 2 bear the same reference numbers increased by one hundred. The hatched region 104 indicates the permanent bonding between the peripheral region 102*a* of the film 102 and the lower film 101.

In a similar manner to FIG. 20, a layer of adhesive transfer-printing ink 110 is positioned on the external surface of the absorbent pad 106 and a protective film 109 is fastened by a tab 109*a* to a transverse edge of the absorbent pad 106, in order to act as a point of hingeing to the flexible film 109, which may for example be a transparent film. This protective film 109 is intended to cover the ink 110, and it has, on its lower face, an adhesive layer against which a peelable protective film 109*b* is pressed. Once the pattern consisting of the ink 110 has been transferred to a given surface, the temporary protective film 109*b* may be removed from the protective film 109, and this protective film 109 may be pressed via its face having the adhesive layer against the printed pattern, in order to immediately remove this pattern from the surface where it was applied and allow it to be repositioned on another surface.

The device in FIG. 21 furthermore includes an additional plastic film 111, of outwardly convex general shape, the peripheral edge 111*a* of which is permanently welded at 112 to the upper face of the film 102, a region of the said peripheral edge 111*a* being connected by a weakened weld 112*a* to the film 102, in order to allow a volume of air 113 lying between the films 111 and 112 to burst when pressure is exerted on the additional film 111.

When the device in FIG. 21 is used, the protective film 109 with its film 109*b* is firstly moved aside, the layer of ink 110 is applied against the surface where it has to be transferred and pressure is exerted on the film 111, thereby causing the volume of air 113 instantly to burst via the weakened weld 112*a* and then causing the reserve of liquid 103 to be crushed, which reserve in turn bursts via the pre-aperture 105, thereby wetting the applicator pad 106 and thus releasing the adhesive transfer-printing ink 110 onto the chosen surface.

It will be noted that the films used in the device of the invention are not necessarily made of plastic, but could be made of metal or of composite materials.

In certain embodiments, the plane support which surrounds the reserve can be used for printing information or patterns. The device may be designed to be overall transparent, opaque or coloured.

Although all the devices illustrated have only a single reserve, several identical or different reserves could be provided on the same device.

The pre-aperture region will be determined so as to burst above a certain resistance threshold which is high enough to guarantee the integrity of the reserve throughout its transportation and storage and which is sufficiently low to be able to be reached by manual pressure.

Yet another advantage of the invention is that it can be used with only one hand.

The support of the device may also be pierced in order to be able to be suspended from a hooking means, for the purpose of its sale.

Although the invention has been described in relation to several particular embodiments, it is quite obvious that it is in no way limited thereto and that it comprises all the technical equivalents of the means described as well as their combinations, provided that these combinations fall within the scope of the invention.

What is claimed is:

1. Device for delivering one or more doses of a fluid product, each dose being contained in a sealed reserve which is defined by an envelope at least partially made of a deformable flexible material, so that a crushing pressure exerted on the reserve causes the envelope to burst in order to release the product contained in the reserve, the envelope being provided locally with at least one region of weakness forming a pre-aperture so as to cause the envelope to burst instantly at the pre-aperture, the flow of product thus being channelled by the pre-aperture in a predetermined orientation, said envelope comprising two films made of at least one of a plastic, a metal and a composite material which are hermetically bonded to each other in a peripheral region in order to define, between the two films, the reserve containing the product characterised in that the peripheral bonding region comprises locally a weakened heat-sealing region forming said pre-aperture, while the rest of the peripheral bonding region is a definitive heat-sealing weld.

2. Device for delivering one or more doses of a fluid product, each dose being contained in a sealed reserve which is defined by an envelope at least partially made of a deformable material, so that a crushing pressure exerted on the reserve causes the envelope to burst in order to release the product contained in the reserve, the envelope being provided locally with at least one region of weakness forming a pre-aperture so as to cause the envelope to burst instantly at the pre-aperture, the flow of product thus being channelled by the pre-aperture in a predetermined orientation, said envelope comprising two films made of at least one of a plastic, a metal and a composite material which are hermetically bonded to each other in a peripheral region in order to define, between the two films, the reserve containing the product, the two films forming the reserve are plane and are superposed, at least one of them including an outwardly domed region in order to define with the other film said reserve, the peripheral region of the films around said domed region extending approximately in the same plane in order to define a peripheral surface for supporting and gripping the device, a layer of material forming an applicator pad which is bonded on said support surface, so as to impregnate the applicator pad with the product via the pre-aperture when the reserve is burst, the applicator pad serving to apply the product to any chosen surface, characterised in that an ink for an adhesive temporary tattoo is positioned on the external face of the applicator pad so that pressure exerted by the user on the reserve causes the envelope to burst via the pre-aperture which in turn moistens the applicator pad and instantly transfers said adhesive temporary tattoo onto a chosen surface.

3. Device according to claim 2 wherein the pre-aperture consists of a prescoring of the envelope in the general form of a cross.

4. Device according to claim 2 wherein the pre-aperture consists of a region of smaller thickness by local deformation of the envelope.

5. Device according to claim 2 wherein the peripheral bonding region comprises locally a weakened heat-sealing region forming said pre-aperture, while the rest of the peripheral bonding region is a definitive heat-sealing weld.

6. Device according to claim 2 wherein the pre-aperture is located on one of the films, approximately at the centre of the reserve.

7. Device according to claim 1 wherein the weakened heat-sealing region is defined between a peripheral portion in the form of a tab of one of the films and a corresponding portion of the other film, said portions being superposed and extending a distance away from the peripheral edge of the reserve.

8. Device according to claim 9 wherein said tab projects into the reserve and is heat sealed in a detachable manner to a corresponding portion of the other film, which has an orifice for delivering the product to the outside when the tab becomes detached under the effect of the pressure of crushing the reserve.

9. Device according to claim 7 wherein the tab projects outside the reserve and is heat sealed in a detachable manner to a corresponding portion of the other film, apart from two lateral edges of the tab which are heat sealed in a definitive manner to the other film in order to define at least one prechannel for opening the reserve.

10. Device according to claim 9 wherein the distal end edge of the tab is welded in a detachable manner in order to define at least one prechannel which can be opened at the end in order to expel the product.

11. Device according to claim 10 wherein the tab extends beyond the corresponding portion of the other film, so as to be able to fold over and fasten in a detachable manner the projecting portion of the tab to the other film, in order to isolate the passage for expelling the product, before its use, from external contaminants.

12. Device according to claim 9 wherein the distal end edge of the tab is heat sealed in a definitive manner to the other film, in order to define at least one closed prechannel and at least one orifice is made through the tab through the corresponding portion of the other film in order to expel the product when the weakened heat-sealing weld becomes detached under the effect of the pressure exerted on the reserve.

13. Device according to claim 12 wherein said at least one expulsion orifice includes a projecting end-piece in order to define a nozzle for spraying the product.

14. Device according to claim 12 wherein each orifice is covered with a protective film which can be moved aside under the effect of the pressure of the product leaving via the orifice, so as to isolate the orifice from external contaminants before use.

15. Device according to claim 12 wherein the expulsion orifice consists of a plurality of micro-orifices arranged in the form of a star, in order to spray the product when it is expelled.

16. Device according to claim 9 wherein the tab includes at least one intermediate line of definitive welding to the other film between its definitively heat-sealed lateral edges, the said intermediate line of welding being approximately parallel to the said lateral edges in order to define a plurality of prechannels for delivering the product.

17. Device according to claim 1 wherein the reserve is in the general form of a hollow bubble containing the product to be delivered.

18. Device according to claim 1 wherein the two films forming the reserve are plane and are superposed, at least one of them including an outwardly domed region in order to define with the other film said reserve, the peripheral region of the films around said domed region extending approximately in the same plane in order to define a peripheral surface for supporting and gripping the device.

19. Device according to claim 18 wherein the two films include a common line of bending which passes right in line with the pre-aperture of the reserve, so that by exerting pressure on the peripheral surface for supporting the device, on either side of the common line of bending, the reserve is crushed by being pinched between two folded-over parts of the device, thereby causing the product to be delivered via the pre-aperture located on the edge of a dihedron formed by the two folded-over parts of the device.

20. Device according to claim 18 wherein a layer of material forming an applicator pad is bonded to the said support surface, so as to impregnate the applicator pad with the product via the pre-aperture when the reserve is burst, the applicator pad serving to apply the product to any chosen surface.

21. Device according to claim 20 characterized by an intercalar free space between the applicator pad and the facing film in order to allow the product released by the reserve to spread out uniformly over the entire surface of the applicator pad.

22. Device according to claim 20 wherein said device includes a protective film which can be moved aside and is bonded to one of the edges of the applicator pad on the external face, in order to cover and isolate the pad from any external element.

23. Device according to claim 20 wherein an ink for an adhesive temporary tattoo is positioned on the external face of the applicator pad so that pressure exerted by the user on the reserve causes the envelope to burst via the pre-aperture, which in turn moistens the applicator pad and instantly transfers the adhesive temporary tattoo onto a chosen surface, in order to form a device for applying an adhesive temporary tattoo.

24. Device according to claim 23 wherein the device includes a protective film which can be moved aside and is bonded to one of the edges of the applicator pad on the external face, in order to cover the ink and to isolate said ink from external elements.

25. Device according to claim 24 wherein the protective film is provided on the external face with a layer of adhesive material covered by a peelable protective film.

26. Device according to claim 23 wherein said device includes an additional film hermetically bonded to the periphery of the support surface on the opposite side from the pre-aperture so as to define a volume of air between the said additional film and the reserve, the said additional film having locally a peripheral weakened-bonding region so that crushing pressure exerted on the said additional film causes, successively or simultaneously, the audible bursting of the volume of air in the weakened-bonding region and the bursting of the reserve via the pre-aperture.

27. Device according to claim 20 characterized in that the applicator pad is hermetically bonded to the peripheral region of one of the films of the envelope.

28. Device according to claim 1 wherein the reserve may contain a liquid, creamy, gelatinous or gaseous product.

* * * * *